(12) United States Patent
Shelton, IV et al.

(10) Patent No.: US 12,685,533 B2
(45) Date of Patent: Jul. 21, 2026

(54) SURGICAL INSTRUMENT POWER SYSTEM WITH INTEGRATED SUPERCAPACITOR POWERED BY LOW VOLTAGE BATTERY

(71) Applicant: CILAG GMBH INTERNATIONAL, Zug (CH)

(72) Inventors: Frederick E. Shelton, IV, Hillsboro, OH (US); Matthew D. Cowperthwait, Cincinnati, OH (US); Shane R. Adams, Lebanon, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 18/959,917

(22) Filed: Nov. 26, 2024

(65) Prior Publication Data

US 2026/0144542 A1    May 28, 2026

(51) Int. Cl.

| | |
|---|---|
| *A61B 17/072* | (2006.01) |
| *A61B 17/00* | (2006.01) |
| *H02J 7/00* | (2026.01) |
| *H02J 7/34* | (2006.01) |
| *H02J 7/50* | (2026.01) |

(52) U.S. Cl.
CPC ............ *A61B 17/072* (2013.01); *H02J 7/345* (2013.01); *H02J 7/50* (2026.01); *H02J 7/855* (2026.01); *A61B 2017/00039* (2013.01); *A61B 2017/00398* (2013.01); *A61B 2017/00734* (2013.01); *A61B 2017/07257* (2013.01); *A61B 2017/07271* (2013.01); *A61B 2017/07285* (2013.01); *H02J 2207/20* (2020.01); *H02J 2207/50* (2020.01)

(58) Field of Classification Search
CPC ........ A61B 17/072; A61B 2017/00039; A61B 2017/00398; A61B 2017/00734; A61B 2017/07257; A61B 2017/07271; A61B 2017/07285; H02J 7/0013; H02J 7/0063; H02J 7/345; H02J 2207/20; H02J 2207/50
See application file for complete search history.

(56) References Cited

U.S. PATENT DOCUMENTS

| | | | |
|---|---|---|---|
| 5,260,637 A | 11/1993 | Pizzi | |
| 5,977,746 A * | 11/1999 | Hershberger | ....... H01M 50/516 |
| | | | 429/149 |
| 8,686,662 B1 * | 4/2014 | Bragg | .................... H02J 9/065 |
| | | | 315/159 |

(Continued)

*Primary Examiner* — Veronica Martin
*Assistant Examiner* — Mobeen Ahmed
(74) *Attorney, Agent, or Firm* — Troutman Pepper Locke LLP

(57) ABSTRACT

A portable surgical instrument having high load conditions and low total energy requirements and a power system suitable for such instruments are provided herein. The power system includes a boost circuit and a supercapacitor. The boost circuit is configured to be powered by a battery underrated for high load conditions and charge the super-capacitor to a higher voltage than the battery provides. The power system can be integral to a main body of the surgical instrument or part of a power module configured to mechanically couple and decouple from a main body of the surgical instrument. The surgical instrument includes a compartment configured to receive one or more battery cells to provide power to the power system. The power system can be compatible for sterilization by high temperature and steam process such as by autoclave.

18 Claims, 9 Drawing Sheets

(56) References Cited

U.S. PATENT DOCUMENTS

| | | | | |
|---|---|---|---|---|
| 8,723,490 B2* | 5/2014 | Moussaoui | ......... | H02M 3/1588 |
| | | | | 323/284 |
| 9,005,230 B2 | 4/2015 | Yates et al. | | |
| 9,050,083 B2 | 6/2015 | Yates et al. | | |
| 9,804,618 B2* | 10/2017 | Leimbach | ................ | B25F 3/00 |
| 10,182,816 B2 | 1/2019 | Shelton, IV et al. | | |
| 10,420,549 B2* | 9/2019 | Yates | ................... | A61B 17/068 |
| 10,973,563 B2* | 4/2021 | Houser | .................... | H02J 7/90 |
| 2005/0096661 A1* | 5/2005 | Farrow | ............. | A61B 17/1628 |
| | | | | 606/167 |
| 2006/0133007 A1* | 6/2006 | Shiue | ....................... | H02P 7/28 |
| | | | | 361/301.2 |
| 2007/0090788 A1* | 4/2007 | Hansford | ................ | H02J 7/485 |
| | | | | 320/107 |
| 2009/0015211 A1* | 1/2009 | Ribellino | ................ | H02M 3/07 |
| | | | | 320/167 |
| 2009/0091302 A1* | 4/2009 | Rusan | .................... | H01G 11/14 |
| | | | | 320/167 |
| 2011/0125138 A1* | 5/2011 | Malinouskas | ......... | A61B 90/90 |
| | | | | 606/1 |
| 2013/0126581 A1* | 5/2013 | Yates | ................... | A61B 17/068 |
| | | | | 227/175.1 |
| 2013/0214025 A1* | 8/2013 | Zemlok | ............ | A61B 17/07207 |
| | | | | 227/175.1 |
| 2014/0107640 A1* | 4/2014 | Yates | ............... | A61B 17/07207 |
| | | | | 227/175.1 |
| 2016/0087460 A1* | 3/2016 | Rich | ..................... | H01M 10/44 |
| | | | | 307/18 |
| 2016/0218404 A1* | 7/2016 | Pedicini | .............. | H01M 50/224 |
| 2016/0249919 A1* | 9/2016 | Savage | ................ | A61B 17/072 |
| | | | | 227/175.1 |
| 2017/0189096 A1* | 7/2017 | Danziger | ........... | A61B 18/1206 |
| 2017/0201120 A1* | 7/2017 | Lisini | ...................... | H02J 7/345 |
| 2017/0231609 A1 | 8/2017 | Gregg | | |
| 2018/0353766 A1* | 12/2018 | Casse | ..................... | A61B 5/686 |
| 2018/0375165 A1* | 12/2018 | Shelton, IV | ......... | A61B 17/072 |
| 2020/0197027 A1* | 6/2020 | Hershberger | ...... | A61B 17/1628 |
| 2020/0297343 A1* | 9/2020 | Satti, III | ........ | A61B 17/320016 |
| 2020/0345357 A1* | 11/2020 | Leimbach | ........ | A61B 17/07207 |
| 2021/0031349 A1* | 2/2021 | Fan | ........................... | B25C 1/06 |
| 2021/0159721 A1* | 5/2021 | Semenov | ................ | H02J 7/345 |
| 2021/0244394 A1* | 8/2021 | Shelton, IV | ..... | A61B 17/00234 |
| 2021/0369273 A1* | 12/2021 | Yates | .............. | A61B 17/07207 |
| 2022/0123581 A1* | 4/2022 | Clarke | ............. | H01M 10/4257 |
| 2023/0082954 A1* | 3/2023 | Hitt | ......................... | H02J 7/345 |
| | | | | 320/135 |
| 2023/0170731 A1* | 6/2023 | Corser | ................... | B60L 50/40 |
| | | | | 700/217 |

* cited by examiner

SURGICAL INSTRUMENT POWER SYSTEM WITH INTEGRATED SUPERCAPACITOR POWERED BY LOW VOLTAGE BATTERY

FIELD

The present invention relates generally to electronic power systems for surgical instruments, and more particularly to power systems utilizing high capacity capacitors for powering a motor of a surgical instrument.

BACKGROUND

Innovation in surgical stapling technology has evolved from manual to power-operated staplers. Manual staplers clamp tissue, deliver staples, and drive a knife blade through mechanical force applied to lever(s) on a handle of the stapler. Powered staplers use an electrically powered motor to drive the knife blade and staples. Powered staplers may also use an electrically powered motor to clamp tissue. Many powered staplers presently in commercial use employ a single use battery which is rated to provide instantaneous current required to drive the motor in a high expected load condition, which typically corresponds to treating thick tissue during a firing stroke. An underrated battery experiences significant voltage sag or deactivates due to internal overcurrent protection during high load conditions, such as firing, and is unable to provide sufficient power to the motor to provide surgical treatment. Because of the required current providing-capacity, batteries which are typically used in powered surgical staplers are overrated in terms of capacity, and only a small fraction of battery capacity is used in a single procedure. Further, the batteries are incapable of withstanding common sterilization processes (e.g., steam by autoclave). Batteries for surgical staplers are therefore disposed of after a single use despite only a small portion of battery capacity being used, thereby resulting in excessive waste.

SUMMARY

Examples of a portable surgical instrument having high load conditions and low total energy requirements are presented herein. Examples of a power system suitable for the portable surgical instrument and those having similar load and energy requirements are presented herein. The power system includes a boost circuit and a supercapacitor. The boost circuit is configured to charge the supercapacitor from a battery such that the supercapacitor is charged to a higher voltage than the battery provides. The power system is configured to provide sufficient power to the surgical instrument to successfully complete a surgical treatment under high load conditions utilizing energy from a battery that is underrated for high load conditions. The power system can be integral to a main body of the surgical instrument or part of a power module configured to mechanically couple and decouple from a main body of the surgical instrument. The surgical instrument includes a compartment configured to receive one or more battery cells to provide power to the power system. The power system can be compatible for sterilization by high temperature and steam process such as by autoclave.

In one embodiment, a surgical instrument includes a compartment, a boost circuit, a supercapacitor, and a motor. The compartment is configured to receive one or more battery cells having a first voltage rating. The boost circuit is configured to receive a voltage input at the first voltage rating and provide a voltage output at a second voltage rating greater than the first voltage rating. The supercapacitor is configured to be charged, via the boost circuit, to approximately the second voltage rating. The motor is configured to be powered by the supercapacitor to provide a surgical treatment. The surgical instrument can include a firing assembly configured to couple to the motor such that the motor is configured to translate the firing assembly in a distal direction to deploy staples from an end effector of the surgical instrument to provide the surgical treatment.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements. The figures depict one or more implementations of the inventive devices, by way of example only, not by way of limitation.

FIG. 8A shows initial charging of the supercapacitor. FIG. 8B shows a simulated sequence of discharging during use under a high load condition and charging by the boost circuit in between usages.

DETAILED DESCRIPTION

Figure 1:
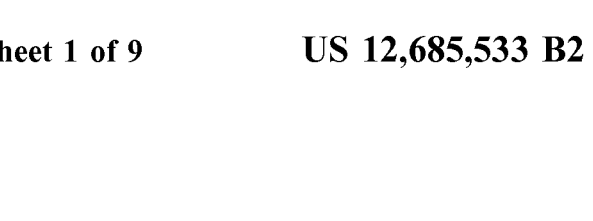
FIG. 1 is a perspective view of an exemplary powered surgical stapler.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives, and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%.

As used herein, the terms "patient," "host," "user," and "subject" refer to any human or animal subject and are not intended to limit the systems or methods to human use, although use of the subject invention in a human patient represents a preferred embodiment. As well, the term "proximal" indicates a location closer to the operator whereas "distal" indicates a location further away to the operator or physician.

As used herein, the term "memory" and "non-transitory computer-readable media" are used interchangeably and are understood to include, but are not limited to, random access memory (RAM), read-only memory (ROM), electronically erasable programmable ROM (EEPROM), flash memory or other memory technology, compact disc ROM (CD-ROM), digital versatile disks (DVD) or other optical storage, magnetic cassettes, magnetic tape, magnetic disk storage or other magnetic storage devices, or any other tangible, physical medium which can be used to store computer readable information.

As used herein, the term "steam autoclave" can include a machine, system, mechanism, or device that is capable of removing harmful microorganisms, pathogens, or bacteria via steam under pressure. As one skilled in the art will appreciate, the nomenclature "autoclave" within the healthcare sector is synonymous with "steam sterilizer." In other words, "steam autoclave" with respect to the present disclosure, can be understood to be any machine, system, mechanism, or device that includes a pressure vessel capable of housing items and subjecting them to steam at a predetermined temperature whilst under pressure to eliminate harmful microorganisms and pathogens on said items.

As used herein, the terms "supercapacitor" and "ultracapacitor" are used interchangeably to refer to a high capacity capacitor or capacitor assembly. Example supercapacitors (ultracapacitors) include, but are not limited to, an electrostatic double-layer capacitor is (EDLC), an electrochemical supercapacitor (ECSC), pseudocapacitors, and the like. The terms "supercapacitor" and "ultracapacitor" are also used herein to refer to a bank, a module, or a pack of multiple interconnected high capacity capacitor cells in series, parallel, or both, in which case, the supercapacitor may include ancillary components such as resistors, transistors, and the like for monitoring and/or balancing the cells.

As used herein, the terms "supercapacitor cell" and "ultracapacitor cell" are used interchangeably herein to refer to an individual cell of a supercapacitor. Said supercapacitor may consist of said supercapacitor cell or may include multiple supercapacitor cells.

As used herein, the terms "boost converter" and "boost regulator" are used interchangeably.

Alternative apparatus and system features and alternative method steps are presented in example embodiments herein. Each given example embodiment presented herein can be modified to include a feature and/or method step presented with a different example embodiment herein where such feature and/or step is compatible with the given example as understood by a person skilled in the pertinent art as well as where explicitly stated herein. Such modifications and variations are intended to be included within the scope of the claims.

Maintaining sterility of a semi-reusable semi-disposable product within the sterile field of the OR, in general, can be challenging due to the extra steps of use as compared to an entirely disposable product. There are reusable surgical staplers currently for sale and in use. For example, the Signia™ Stapling System from Covidien is a non-sterile wipe down device that is placed into a sterile clam-shell for use. Aseptic transfer into the sterile field is accomplished by dropping the Covidien surgical stapler from outside the sterile field into the open shell held by someone inside the sterile field, which can be cumbersome. Other commercial surgical staplers have been available with a disposable body and a reusable non-sterile battery which also required a cumbersome transfer into the sterile field and further issues with battery interchange once inside the sterile field.

Unlike a battery, a supercapacitor can be sterilized by autoclave, eliminating many of the sterile-field transfer problems associated with a reusable battery or product containing a reusable battery. However, capacitors have lower capacity per volume compared to a battery, and a charged supercapacitor loses a great deal of stored energy (25-30%) while being exposed to high temperatures in the autoclave. Once sterile, charging a supercapacitor inside the sterile field is quite challenging due to the difficulty of maintaining sterility of a power source for charging the supercapacitor. Example surgical staplers presented herein provide an alternative semi-reusable semi-disposable product which may address the aforementioned problems with previous semi-reusable semi-disposable products.

A power system for a surgical stapler is presented herein which includes a supercapacitor and a battery. The supercapacitor is rated to deliver voltage, instantaneous current, and total energy required by the motor during a firing stroke. The battery has a voltage rating sufficient to power control electronics, energy capacity sufficient to power the surgical stapler throughout an entire procedure, and a current rating sufficient to charge the supercapacitor in a timely manner while maintaining sufficient voltage to power control electronics. The battery may consist of a single battery cell or may include more than one battery cell. The supercapacitor and the battery may be sterilized in two differing manners and combined within the operating room for use. The supercapacitor is housed in a reusable portion and includes control electronics for charging the supercapacitor. The battery may be sterilized in a manner that is compatible with the battery chemistry. The reusable portion of the surgical stapler and the battery may be combined in an operating room (OR) to work together, while both portions are sterile, for interaction with the sterile surgeon.

Autoclave steam sterilization is a common sterilization method for hospitals. The autoclave performs sterilization at around 270° F. and 15-30 psi pressure. The saturation time is around 5 minutes of the overall 15-30 min cycle. Max storage temperature for a CR123a battery is 140° F. for safety reasons because the battery vents at elevated temperatures. Batteries have the high potential of venting within the 270° F. temperature of autoclave, and such venting contaminates the entire autoclave. Capacitors or supercapacitors do not have this safety risk because they do not vent during autoclave sterilization.

CR123a battery cells can be sterilized via ethylene oxide (ETO) sterilization and irradiation, but those processes are not usually available to hospitals in their regular processes. The current Echelon™ 3000 and older Echelon™ powered plus surgical staplers utilize (four) CR123a battery cells in a battery pack in order to provide the voltage and current necessary for operating a 12 VDC motor. CR17345 battery cells are similarly used in other surgical staplers. These battery packs have much more energy capacity than is needed during a single procedure and are rated based on the voltage and current requirements for proper motor operation. The battery packs are not re-sterilizable at the hospital, and it is considered non-green to throw away those batteries and electronics while using so little of them.

In some embodiments presented herein, the reusable portion of the surgical stapler includes a control board sealed in a reusable housing that can be taken from one procedure, set to be re-sterilized thru an autoclave, and then returned to the next OR for reuse up to 20-60 times. For each procedure, the battery consists of a single battery cell (e.g., CR123a) that is disposed of after a single use.

In one embodiment, a single CR123a is rated 3.2 V to 3.3 V and approximately 1.4 A while the motor requires 12 V and 5 A. To accommodate this, the single battery cell is used to charge the supercapacitor to 12 V through a boost circuit, and the charged supercapacitor is rated to provide approximately 5 A with acceptable voltage drop during a firing stroke. One challenge with charging the supercapacitors is that the boost circuit electronics are powered from the CR123a and the high battery current required to charge the supercapacitors may result in a voltage sag on the battery, which may cause the boost circuit to go offline and therefore stop charging the supercapacitors. Additionally, batteries have a thermal limiter that acts like a fuse to permanently deactivate the battery cell due to an overcurrent condition or prolonged high battery current.

Examples presented herein include an overcurrent limiter circuit configured to prevent voltage sag on the battery which would result in deactivation of the boost circuit. The overcurrent limiter may also be configured to prevent activation of internal overcurrent protection of a boost converter of the boost circuit. The battery may also directly provide power to control electronics of the surgical stapler, including motor drive control. In such instances, the overcurrent limiter may also be configured to prevent voltage sag on the control electronics which would result in deactivation or malfunction of the control electronics. In some embodiments, the overcurrent limiter may include a resistance of about 3 (2 to about 5 (2 in series with the boost regulator to regulate the max draw from the battery but also maximized the speed at which the supercapacitor can be charged. In some embodiments, the overcurrent limiter may include an active control configured to sense battery and/or boost regulator current and impede current to an acceptable level based on the sensed current.

Upon initial connection of the battery to the boost regulator, the battery charges the supercapacitors within an initial time period short enough as to not encumber surgical room procedures and long enough so that current from the battery is limited to acceptable levels, for instance between about 60 seconds and about 120 seconds. Preferably, the voltage across the supercapacitors is about 11 V or more at the end of the initial charging time period. After firing, the super- capacitors are recharged during an intermediate time period short enough as to not to cause a delay in a subsequent motor operation, but long enough so that current from the battery is limited to acceptable levels, for instance between about 30 second and about 90 seconds. During this intermediate time period, a user may reload the end-effector of the stapler for a subsequent stapling action, therefore the intermediate time period can be as long as the expected time to unclamp, unload, and reload the end effector without encumbering surgical room procedures.

Given the low voltage and current rating of the battery, the higher voltage and current rating of the supercapacitors, and the timing requirements for charging, boost circuits generally are not plug-and-play in this application. Examples presented herein are designed to prevent battery deactivation by the battery thermal limiter, prevent damage to the boost regulator due to overcurrent, and prevent temporary deactivation of the boost regulator due to voltage lag. Examples presented herein include a boost regulator configured to provide a 12 V output; alternatively, a boost regulator configured to provide a 15 V output could be utilized in order to charge the supercapacitors to an initial 80% of capacity faster in the initial time period to reduce the initial time period causing delay before first use of the surgical stapler. Optionally, the power circuit can include a power accumulator on the input of the boost regulator to reduce the likelihood of battery voltage lag impacting operation of the boost regulator.

The boost regulator, supercapacitor, and related electronics can be located in the reusable portion of the surgical stapler.

One example includes a 2 Farad (F) supercapacitor (which includes five 10 F supercapacitor cells in series to achieve a 12 V rating) enables the Echelon™ 3000 to fire 1.1 to 1.75 times over stress through a 60 mm firing stroke or 2 to 3 times in air firings through a 60 mm firing stroke. In these tests, the current from the battery maxes out at 2 A while charging during and recovering from a firing. The max current draw from the boost regulator is 6 to 8 A during initial charging from a completely uncharged state. This is utilizing a single CR123a and does not exceed its internal thermal limiting fuse. The recovery time for the system after a single firing is 20-25 sec. Which is less than the minimum time needed to release, remove, reload, re-insert and then reposition for the next firing. The initial charge time from initial assembly to ready-to-use is 50-60 sec. In this example, five power systems, each including the printed circuit board assembly (PCBA), which includes the boost converter and related electronics, and the supercapacitor, successfully survived 20 autoclave full use cycles (273° F. for 15 minutes) with no failures.

The battery, which can consist of a single CR123a, can be gamma sterilized in an individual blister pack and handled sterile with the autoclave semi-reusable control board and electronics and the sterile disposable handpiece. By using a single CR123a disposable with each surgery and 1 PCBA for 20 procedures, waste and cost of goods sold can be reduced compared to existing power surgical stapler products.

FIG. 1 is a perspective view of an exemplary surgical stapler 10 including a handle 20, a shaft 24, and an end effector 40. The handle 20 is configured to be grasped, manipulated, and actuated by a clinician. The shaft 24 is sized, shaped, and otherwise configured to extend through a body opening of the patient. The end effector 40 is configured deliver staples 45. The end effector 40 may also be configured to cut tissue within the body of the patient.

The handle 20 can include a closure trigger 21, a firing trigger 22, and a grip 23 sized such that a clinician can single-handedly hold the surgical stapler 10 by the grip 23 while manipulating the closure trigger 21 or the firing trigger 22. The closure trigger 21 is operably connected to a motor disposed within the handle 20 such that when the closure trigger 21 is pulled, the motor is driven to cause the end effector 40 to clamp tissue. Alternatively, the closure trigger 21 can be mechanically coupled to the end effector 40 such that when the closure trigger 21 is pulled, the end effector 40 moves to clamp tissue without the aid of a motor. The firing trigger 22 is operably connected to a motor 65 (FIG. 7) disposed within the handle 20 such that when the firing trigger 22 is pulled, the motor 65 is driven to cause the end effector 40 to deploy staples 45 into the clamped tissue and may also cut the clamped tissue.

The handle 20 can further include additional features such as a firing trigger lock mechanism (not illustrated) which can be manipulated to prevent actuation of the firing trigger 22, a power module 30 configured to provide electrical power to the motor and other electrical components of the powered surgical stapler 10, a closure release button 25 which can be manipulated to release the end effector 40 and the closure trigger 21 from the clamped position, a home button 26 that can be pressed to cause the motor to move a knife (not illustrated) of the end effector 40 in the proximal direction PD to a home position, a manual override 27 including a mechanical actuator which can be manipulated to mechanically move the knife proximally to the home position, articulation buttons 28 that can be pressed to cause a motor to articulate the end effector 40 at an articulation joint 44 so that the end effector 40 is at an angle with a longitudinal axis S-A of the shaft 24, a rotatable nozzle 29 configured to be rotated so that the shaft 24 and end effector 40 rotate about the shaft axis S-A, a display 31 (FIG. 2) configured to display information related to the surgical stapler, variations thereof, other compatible features of a powered surgical stapler handle, and combinations thereof.

The end effector 40 includes an anvil 41 and a staple jaw 42 opposite the anvil 41. The anvil 41 and staple jaw 42 are illustrated in an open position. The anvil 41 and staple jaw 42 can be moved toward each other to move the end effector 40 to a clamped configuration. For instance, tissue (not illustrated) can be positioned between the anvil 41 and staple jaw 42 in the open position, and the anvil 41 can rotate toward the staple jaw 42 to clamp the tissue.

When the end effector 40 is in the clamped configuration, the firing trigger 22 can be pulled to cause deployment of staples 45 from the cartridge 43 and may also cause cutting of tissue. The surgical stapler 10 can include a firing assembly configured to couple to the motor 65 such that the motor 65 is configured to translate the firing assembly in a distal direction DD to deploy the staples 45 from an end effector 40 of the surgical instrument 10 to provide a surgical treatment.

Portions of the surgical stapler 10 may be detachable and interchangeable. Staples 45 may be housed in a staple cartridge 43 that is detachable from the end effector 40. The end effector 40 may be detachable from the shaft 24, and the shaft 24-handle 20 combination may be configured for use in connection with interchangeable end effectors. At least a portion of the shaft 24 including the end effector 40 may be detachable from the handle 20, and the handle 20 may be configured for use in connection with interchangeable shaft assemblies having different shaft lengths and/or different end effectors attached thereto. The power module 30 may be detachable from the handle 20.

Figure 2:
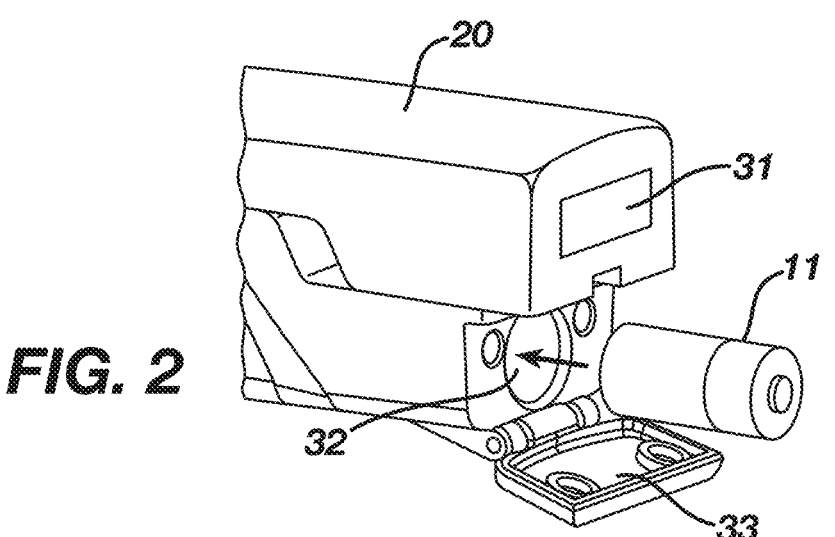
FIG. 2 is an illustration of a handle portion of a main body of an exemplary powered surgical stapler having an integrated power system and a compartment for a battery cell.

FIG. 2 is an illustration of a handle portion 20 of a main body of an exemplary powered surgical stapler having an integrated power system and a compartment 32 for a battery 11. The handle 20 can include a compartment hatch 33 which can be closed to hold the battery 11 in the handle 20. The main body, or at least the handle portion, can be sterilized under conditions unsuitable for the battery 11 such as by steam sterilization with an autoclave. Under intended use, the battery 11 is removed from the main body after a procedure so that the main body can be sterilized. The power system includes a boost converter and a supercapacitor. For instance, the components of the power module 30, including the supercapacitor 34, illustrated in FIG. 4 can be integrated into the main body such that the power system cannot be separated from the main body without damaging the main body or otherwise using the surgical stapler contrary to intended use of the surgical stapler.

Upon first use of the main body, the supercapacitor 34 may be fully discharged. Upon insertion of the battery 11 and closure of the hatch 33, the battery 11 becomes connected to the power system and may begin to charge the supercapacitor 34 from a fully discharged state to a non-zero threshold voltage that is preferably sufficient for the supercapacitor 34 to provide energy to the surgical stapler 10 to perform a surgical treatment. Once at the threshold voltage, the display 31 may provide an indication that the surgical stapler 10 is ready for use. During an operating room procedure, energy is discharged from the supercapacitor 34 during each high load surgical treatment (e.g., stapler firing stroke), and recharged, using energy of the battery 11, in between each high load surgical treatment. Preferably, the supercapacitor retains at least half of its fully charged voltage following each high load surgical treatment. This provides power stability to the surgical stapler 10 and potentially reduces recharge time between each high load surgical treatment. At the end of the procedure, the battery 11 has discharged a larger proportion of its energy than in many presently available surgical stapler systems, resulting in less battery waste. The battery 11 may be disposed of or separately sterilized as appropriate for the battery chemistry. At the end of the procedure, it may be advantageous to discharge the supercapacitor 34 prior to sterilization. In some embodiments, the surgical instrument includes a discharge circuit configured to discharge the supercapacitor 34 automatically after battery removal or may include a user input which can be operated to cause the supercapacitor 34 to discharge. If the supercapacitor 34 is not discharged following completion of a surgical procedure, it may lose some energy during sterilization following the procedure. If the supercapacitor 34 remains partially charged following sterilization, the initial charging time period of a subsequent use of the power system may be reduce.

Figure 3A:
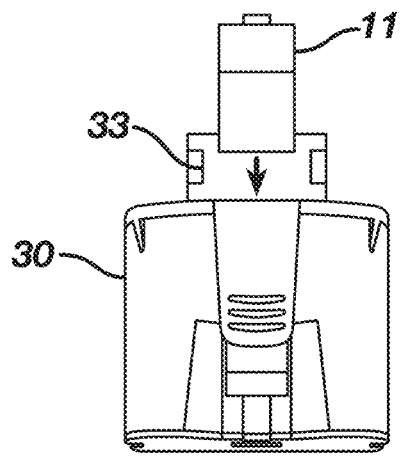
FIG. 3A is an illustration of an exemplary power module housing a power system and including a compartment for a battery cell.
Figure 4:
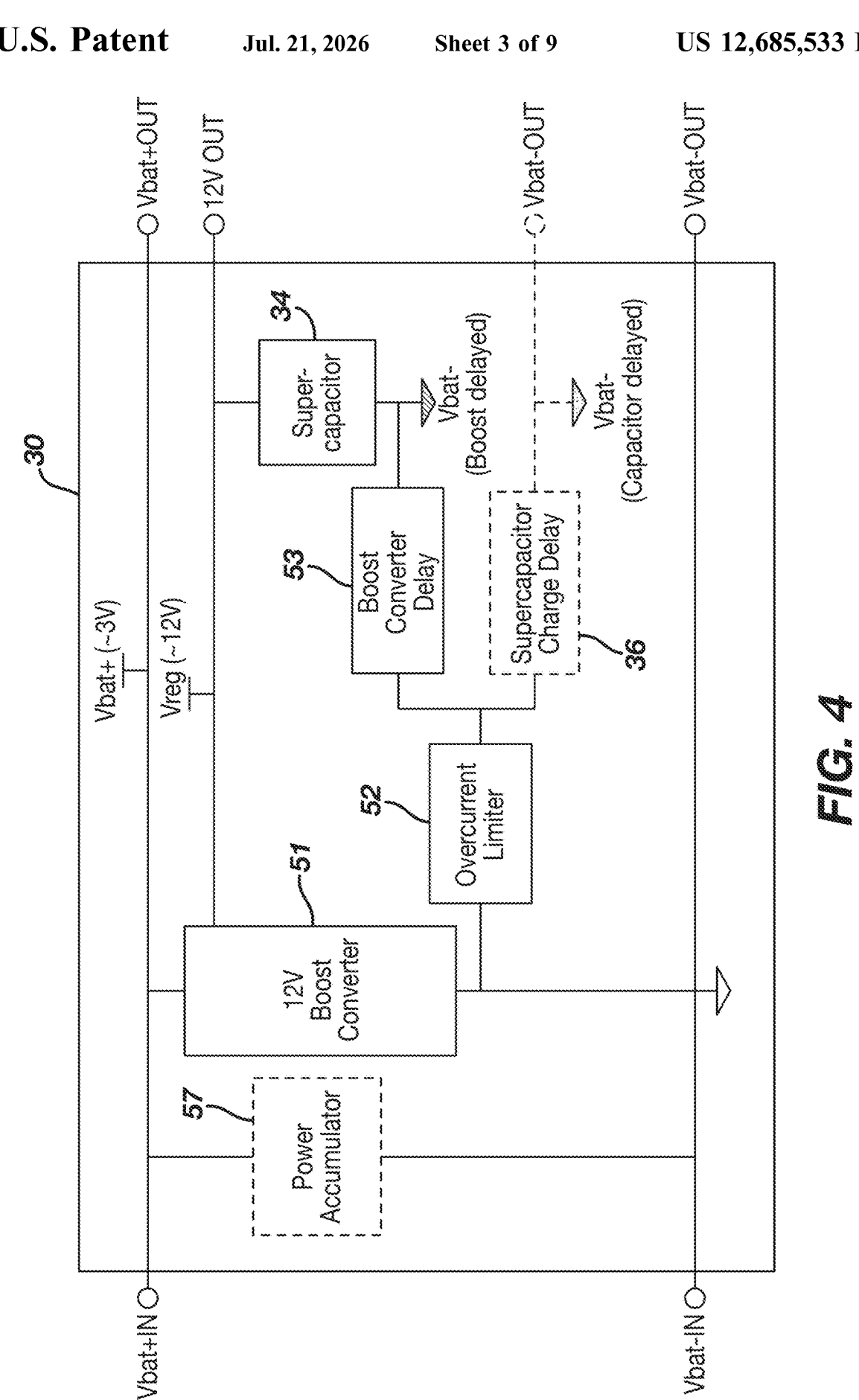
FIG. 4 is a block diagram of an exemplary power module.

FIG. 3A is an illustration of an exemplary power module 30 which houses a power system and includes a compartment 32 for a battery 11. The power module 30 can include a compartment hatch 33 which can be closed to hold the battery 11 in the power module 30. The power module 30 can be sterilized under conditions unsuitable for the battery 11 such as by steam sterilization with an autoclave. Under intended use, the battery 11 is removed from the power module 30 after a procedure so that the power module 30 can be sterilized. The power module 30 can include a boost converter 51, a supercapacitor 34 and associated components as illustrated in FIG. 4.

Figure 3B:
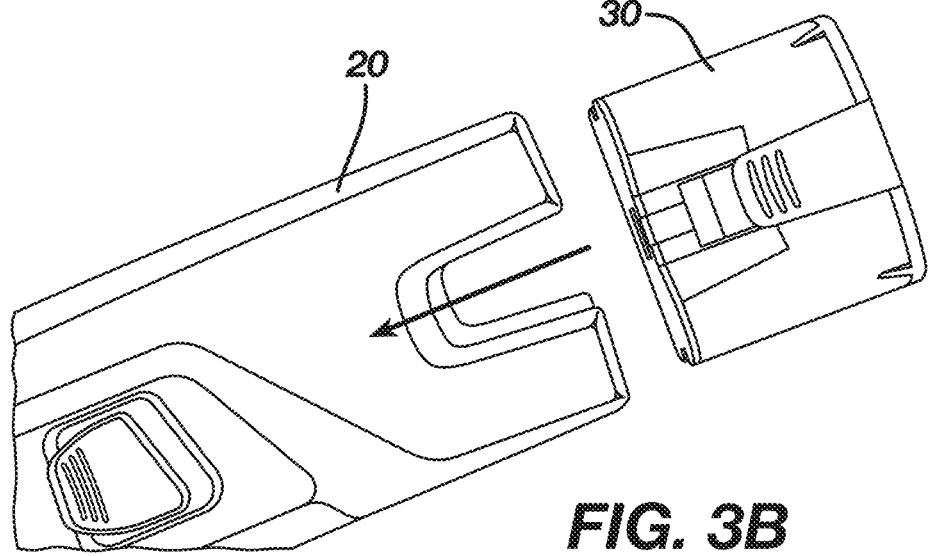
FIG. 3B is an illustration of the power module of FIG. 3A being coupled to a handle portion of a main body of an exemplary powered surgical instrument.

FIG. 3B is an illustration of the power module 30 of FIG. 3A being coupled to a handle portion 20 of a main body of an exemplary powered surgical stapler 10. The power module 30 may be detached from the handle 20 and separately sterilized. The power module 30 can be configured to withstand temperatures greater than 135° F., preferably at least 270° F., and pressures greater than 15 psi. The power module 30 can otherwise be configured to withstand typical autoclave sterilization temperature and pressure as understood by a person skilled in the pertinent art.

Upon first use of the power module 30, the supercapacitor 34 may be fully discharged and may be charged to a non-zero threshold voltage as discussed in relation to FIG. 2. The power module 30 may also include a visual indicator or other display similar to display 31 in FIG. 2 to provide an indication that the power module 30 is charged and ready for use. During an operating room procedure, the supercapacitor 34 is repeatedly discharged and charged as discussed in relation to FIG. 2. At the end of the surgical procedure, it may be advantageous to discharge the supercapacitor 34 prior to sterilization. In some embodiments, the power module 30 includes a discharge circuit configured to discharge the supercapacitor 34 automatically after battery removal or after disconnection of the power module 30 to the main body, or the power module 30 may include a user input which can be operated to cause the supercapacitor 34 to discharge. If the supercapacitor 34 is not discharged following completion of a surgical procedure, it may lose some energy during sterilization following the procedure. If the supercapacitor 34 remains partially charged following sterilization, the initial charging time period of a subsequent use of the power system may be reduce.

Referring collectively to FIGS. 2 and 3A, the compartment 32 and hatch 33 can include a pair of battery input contacts Vbat+IN, Vbat−IN (FIGS. 4, 5A, and 5B) configured to make electrical connection to positive and negative terminals of the battery 11. The battery 11 is illustrated as a single battery cell. Alternatively, the battery can include multiple battery cells and optionally related electronics of a battery pack. Preferably, the battery 11 has exactly one or exactly two battery cells. The battery 11 can include CR123a, CR17345, CR2 lithium, or other suitable battery cell(s) as understood by a person skilled in the pertinent art. In one embodiment, the compartment 32 is configured to receive a single CR123a cell as the battery 11. In another example, the compartment 32 is configured to receive a single CR17345 cell as the battery 11. In yet another example, the compartment 32 is configured to receive a single CR2 lithium cell as the battery 11.

The display or visual indicator 31 may include a screen configured to display text or images or may simply include one or more lights (e.g., light emitting diodes). The power module 30 illustrated in FIG. 3A and/or handle 20 in FIG. 3B may include a visual indicator similar to the display 31 shown in FIG. 2. The display 31 can be configured to provide visual indication related to the status of the power system. For instance, the display 31 may provide a visual indication that the power system is ready to provide sufficient power to the surgical instrument to operate under a high load condition such as driving the motor 65 (FIG. 7) through a firing stroke. The display 31 may also provide a visual indication of other information relating to the status of the power system such as, but not limited to, an indication that the supercapacitors are in an initial charging mode, the supercapacitors are charging in between high load conditions, the voltage of the supercapacitors, the energy stored in the supercapacitors, a countdown until charging is complete, an error condition, etc.

FIG. 4 is a block diagram of electrical components of an exemplary power module 30.

Figure 5A:
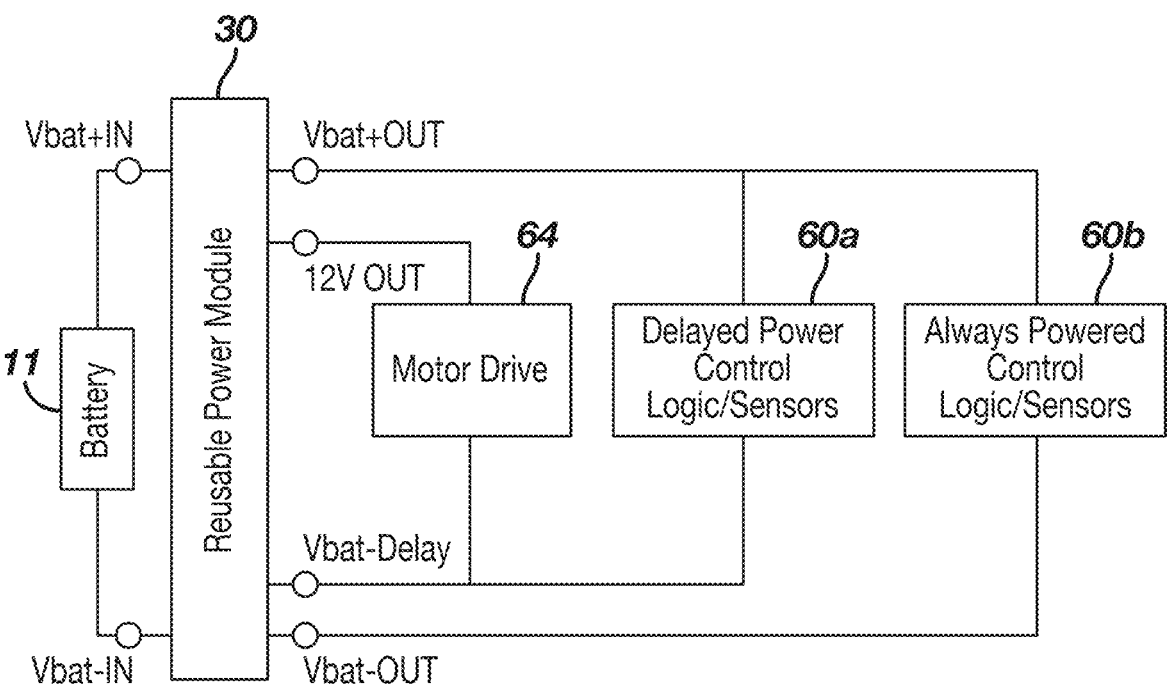
FIGS. 5A and 5B are block diagrams of connections schemes of the exemplary power module.
Figure 5B:
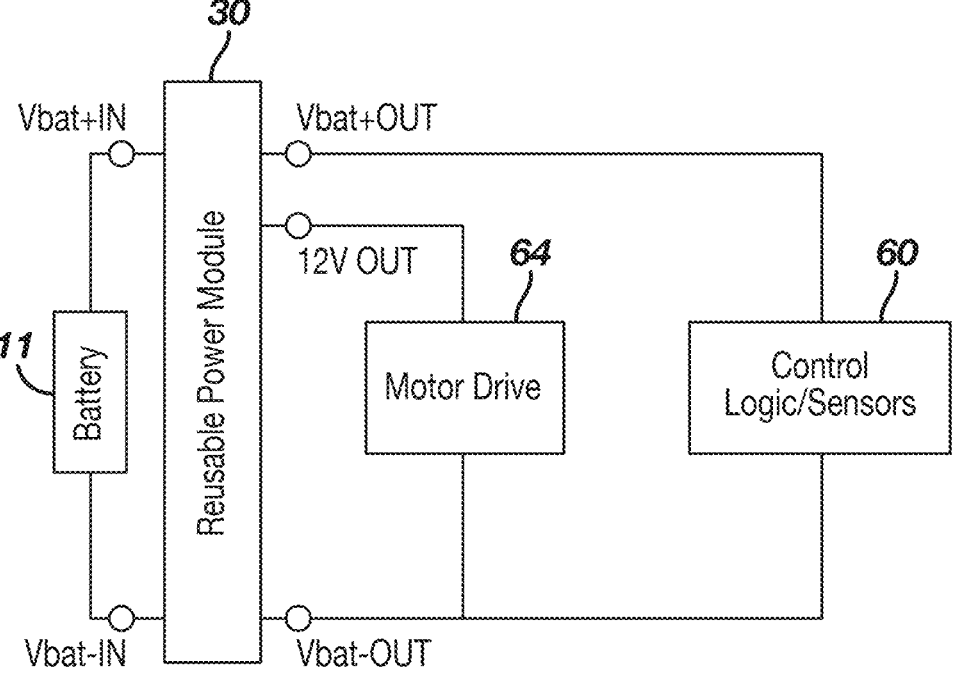

FIGS. 5A and 5B are block diagrams of connections schemes of the exemplary power module 30 to the downstream circuitry of the surgical instrument 10.

Referring collectively to FIGS. 3A, 3B, 4, 5A, and 5B, the power module 30 is configured to mechanically and electrically couple to, and decouple from, the main body. As mentioned above, the power module 30 includes a pair of battery input contacts Vbat+IN, Vbat-IN configured to make electrical connection to positive and negative terminals of the battery 11. The power module further includes a pair of boost voltage output contacts 12VOUT, Vbat-OUT or Vbat-Delay configured to provide electrical contact to the positive and negative terminals of the supercapacitor 34 (FIG. 4) to electronics in the main body (e.g., handle 20). Optionally, the power module 30 can include a pair of battery output contacts Vbat+OUT, Vbat-OUT configured to provide connection of the positive and negative terminals of the battery 11 to the handle 20 of the main body. Optionally, the power module 30 includes one or more delayed power output contacts Vbat-Delay configured to provide delayed power connection from the battery 11, supercapacitor 34, or both, to the electrical circuits in the main body of the surgical instrument 10. The display 31 can include a visual indicator configured to indicate power connection to the main body via the delayed power output contact Vbat-Delay (i.e., activation of the delayed power output contact following a supercapacitor charge delay time period).

As illustrated in FIG. 4, the power module 30 includes a boost converter 51, current limiter 52, boost converter delay 53, and supercapacitor 34. Electronics of the power module 30, including the boost converter 51, which are used to charge the supercapacitor 34, are referred to herein as "boost circuit."

For the sake of illustration, the boost converter 51 as illustrated is configured such that the boost circuit provides a 12 V rated output voltage Vreg and the battery 11 has a rated output of 3.3 V. The boost converter 51 can be rated to provide an output voltage that is between approximately 3 and approximately 5 times the battery voltage. For instance, the boost converter 51 may be rated to provide an output voltage between approximately 9 volts and approximately 15 volts for an input voltage of 3 volts; provide an output voltage between approximately 10 volts and approximately 16.5 volts for an input of 3.3 volts; provide an output voltage between 15 volts and 25 volts for an input of 5 volts; and ranges of output voltages therebetween given an input voltage between 3 volts and 5 volts. The boost circuit output voltage rating can be approximately 4 times the battery voltage rating.

As mentioned above, the power module 30 is reusable and may be sterilized under high pressure, temperature, and humidity conditions. Under such sterilization conditions, the supercapacitor 34 is undamaged, however is likely to lose a significant amount of stored energy during sterilization. Upon initial connection of battery 11 to the battery input contacts Vbat+IN, Vbat−IN, the boost converter 51 may require an initial time period, e.g., a soft-start time period, to be able to provide an output. The boost converter delay circuit 53 is configured to delay electrical connection of the supercapacitor 34 to the output of the boost converter 51 to allow the boost converter 51 to provide its output to the supercapacitor 34. The boost circuit of the power module 30 can optionally include a power accumulator 57 configured to reduce voltage sag of the battery 11 under high load conditions of the boost converter 51. The power accumulator 57 may also charge or otherwise store energy during the first time period. Thus, initiation of supercapacitor charging is delayed for a first time period following electrical connection of the battery 11 to the voltage input of the boost circuit. In one embodiment, the first delay time period is greater than the soft-start time period and less than about 1 second.

After the first time period is elapsed, the boost converter delay circuit 53 connects the supercapacitor 34 to the output of the boost converter 51 via the current limiter 52. The current limiter 52 includes one or more electrical components or circuits configured to limit current output of the boost converter to a threshold value. In one embodiment, the current limiter 52 is a simple resistor with a resistance value chosen to limit the current output of the boost converter to be equal to or less than the threshold value. Alternatively, the current limiter 52 includes a circuit configured to provide a constant current output from the boost converter 51 when the voltage output of the boost converter 51 is less than the rated voltage output of the boost converter 51. In this manner, the boost circuit is configured to initially charge the supercapacitor in a constant current mode with a constant current output to approximately the rated voltage output of the boost converter 51. The constant current output can be between approximately 200 milliamperes (mA) and approximately 2 A. A simpler, potentially less expensive and less bulky circuit can be used to provide the lower constant current outputs, while the higher constant current output provides a faster charging time of the supercapacitor 34. The constant current output can be between approximately 1 A and approximately 2 A, between approximately 300 mA and approximately 1 A, between approximately 400 mA and approximately 1 A, between approximately 500 mA and approximately 1 A, between approximately 600 mA and approximately 1 A, between approximately 700 mA and approximately 1 A, between approximately 800 mA and approximately 1 A, between approximately 900 mA and approximately 1 A, between approximately 200 mA and approximately 500 mA, between approximately 300 mA and approximately 500 mA, between approximately 400 mA and approximately 500 mA, between approximately 400 mA and approximately 600 mA, between approximately 800 mA and approximately 1.2 A, between approximately 1 A and approximately 1.4 A, between approximately 1.4 A and approximately 1.6 A, between approximately 1.6 A and approximately 1.8 A, or between approximately 1.8 A and approximately 2 A.

The supercapacitor 34 can have a capacitance of between approximately 1 farad (F) and approximately 3 F, between approximately 1.5 F and approximately 2.5 F, or approximately 2 F. In one embodiment, the supercapacitor is rated 2 F. The supercapacitor 34 can have a voltage rating between approximately 12 V and 15 V. In one embodiment, the voltage rating of the supercapacitor is equal to or greater than the rated voltage output of the boost circuit. The time to charge the supercapacitor 34 from an uncharged condition (e.g., 0 V) approximately the rated output voltage of the boost convert 51 is dependent on the capacitance of the supercapacitor 34 and the charging current. For instance, a 2 F capacitor charged by a constant current of 1 A can be charged from 0 V to 12 V in approximately 24 seconds. The boost circuit can be configured to charge the supercapacitor from 0 V to approximately the rated output voltage of the boost converter 51 between approximately 10 seconds and approximately 120 seconds, between approximately 10 seconds and approximately 20 seconds, between approximately 20 seconds and approximately 120 seconds, between approximately 20 seconds and approximately 30 seconds, between approximately 30 seconds and approximately 40 seconds, between approximately 40 seconds and approximately 50 seconds, between approximately 50 seconds and approximately 60 seconds, between approximately 60 seconds and approximately 90 seconds, or between approximately 90 seconds and approximately 120 seconds.

The power module 30 can optionally include a supercapacitor charge delay circuit 36 configured to delay connection of the optional delayed power output contact Vbat-Delay to one or more power sources such as the battery 11, the boost circuit, the supercapacitor 34, or a combination thereof. As illustrated, the Vbat-Delay terminal is a negative, or reference terminal for the battery 11, the boost circuit, and the supercapacitor 34. Configured as such, power output from the power module 30 to circuits of the surgical instrument 10 powered via the delayed power output contact Vbat-Delay are disconnected from all power sources of the power module 30 during supercapacitor charging. The boost circuit and the output terminals of the power module 30 can modified to provide additional or alternative delayed power output contact(s) as understood by a person skilled in the pertinent art. For instance, the boost circuit can be modified to include a supercapacitor charge delay circuit upstream of the battery terminal Vbat+out, between the supercapacitor positive terminal Vreg and positive boost voltage output contact 12VOUT. In some embodiments, the supercapacitor charge delay circuit 36 acts only to delay initial connection of the supercapacitor to the delayed power output contact Vbat-Delay and does not disconnect the supercapacitor from the Vbat-Delay until an event occurs indicating that the surgical procedure is completed such as the battery 11 begin removed or the power module 30 being removed from the handle 20.

Once the supercapacitor is initially charged, the circuitry of the surgical instrument can be configured such that the supercapacitor retains a majority of its stored energy during a surgical procedure. For instance, the supercapacitor 34 can be configured to retain a voltage of at least 50%, or more preferably between 70% and 90%, of its charged voltage (i.e., approximately the rated output voltage of the boost circuit) upon completing of a surgical treatment. The boost circuit is configured to recharge the capacitor to its charged voltage within approximately 1 second and approximately 60 seconds following completion of the surgical treatment. The boost circuit can be configured to recharge the capacitor within approximately 1 second and approximately 2 seconds, within approximately 2 seconds and approximately 60 seconds, within approximately 2 seconds and approximately 30 seconds, within approximately 2 seconds and approximately 10 seconds, within approximately 10 seconds and approximately 20 seconds, within approximately 20 seconds and approximately 30 seconds, within approximately 30 seconds and approximately 40 seconds, within approximately 40 seconds and approximately 50 seconds, or within approximately 50 seconds and approximately 60 seconds.

As illustrated in FIGS. 5A and 5B, the power module 30 receives power from battery 11 and provides power to a motor drive 64 and control logic and sensors 60, 60a, 60b which operate the surgical instrument 10. FIG. 5A shows an embodiment including the optional delayed power output terminal Vbat-Delay. In this embodiment, the control logic and sensors 60 of the surgical instrument 10 are divided between delayed power circuits 60a and always powered circuits 60b. The delayed power circuits 60a receive power from the power module 30 via the delayed power output terminal Vbat-Delay, while the always powered circuits 60b are connected to the battery 11 via the boost circuit without a delay associated with supercapacitor charging. In the illustrated embodiment, the control logic and sensors 60, 60a, 60b are powered from the battery 11 rather than from the supercapacitor 34. Alternatively, some or all of the control logic and sensors 60, 60a, 60b may be powered from the positive boost voltage output contact 12VOUT rather than the battery output terminal Vbat+OUT. FIG. 5A shows the motor drive circuit 64 connected to the positive boost voltage output contact 12VOUT and the delayed power output contact Vbat-Delay. FIG. 5B shows an alternative configuration in which the motor drive circuit 64 is connected to the positive boost voltage output contact 12VOUT and the negative power output contact Vbat-OUT.

Figure 6:
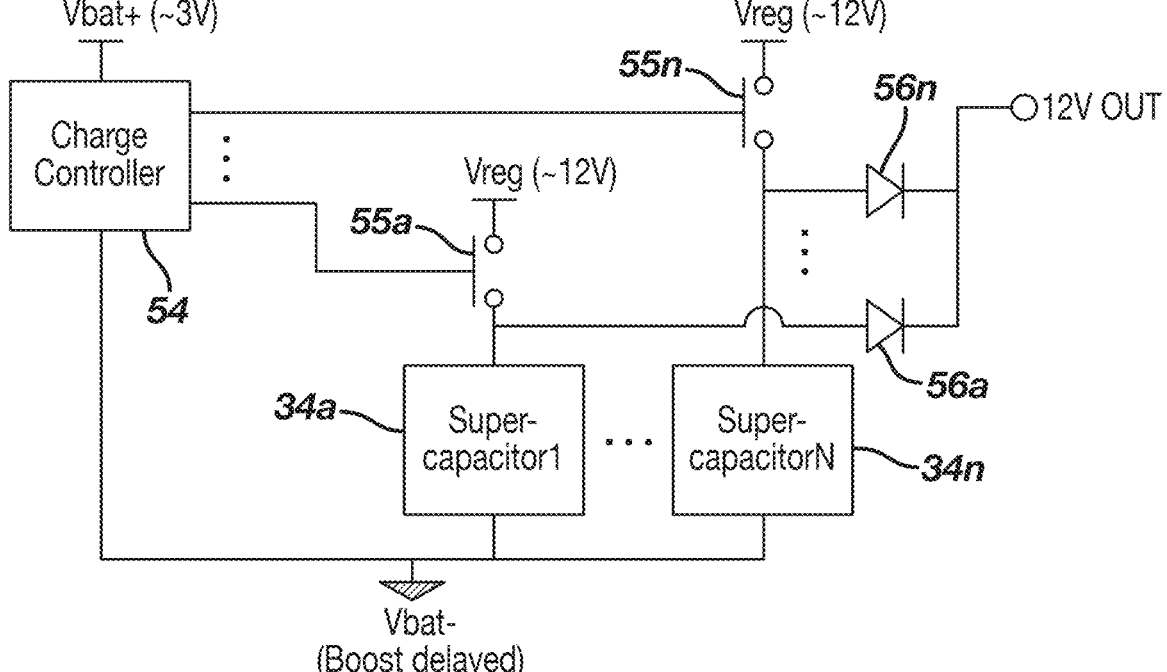
FIG. 6 is a block diagram of a sequential capacitor charging circuit which can be incorporated into a power module to sequentially charge parallel supercapacitors.
Figure 7:
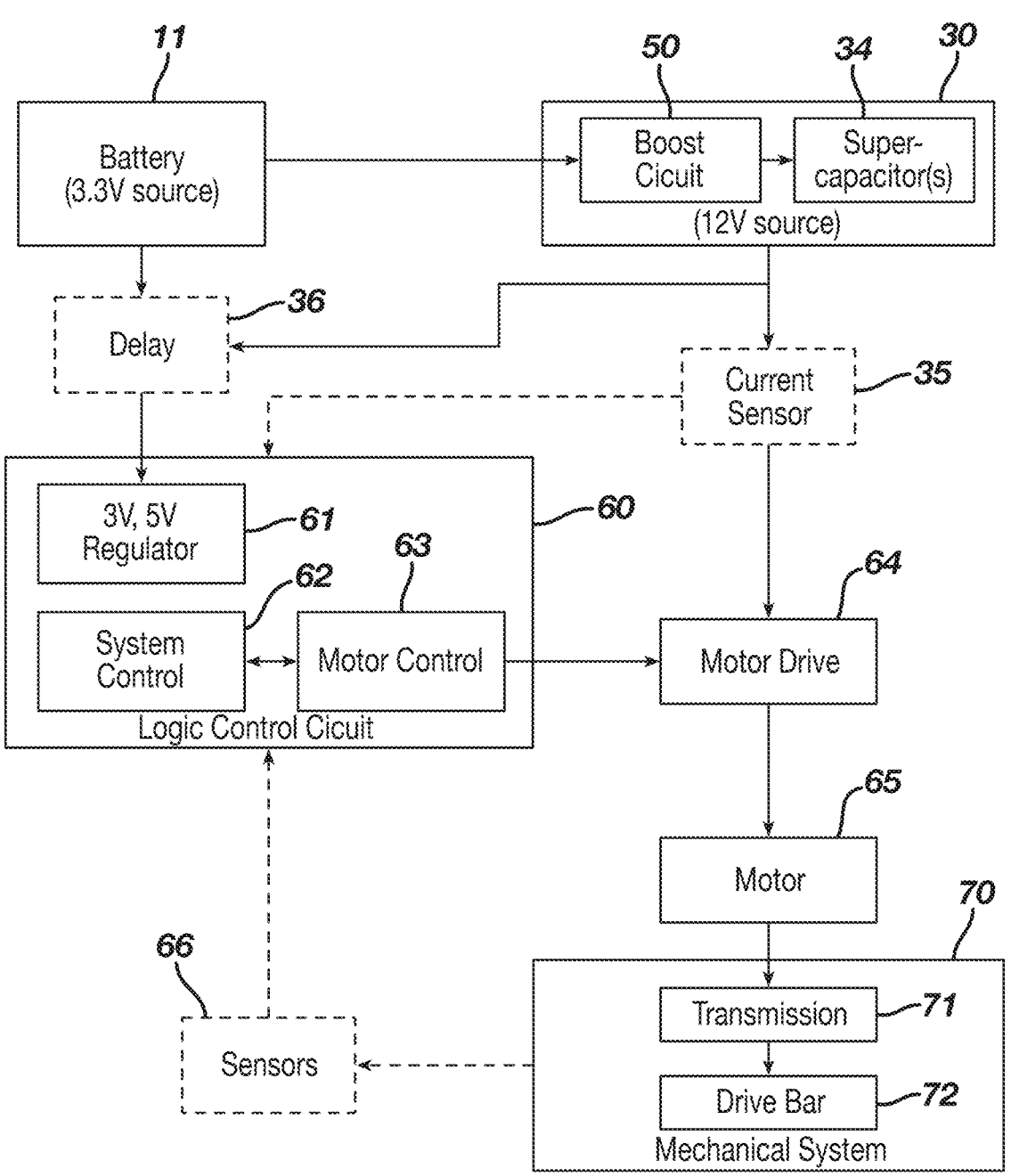
FIG. 7 is a block diagram of electrically powered components of an exemplary powered surgical stapler.

FIG. 6 is a block diagram of a sequential capacitor charging circuit which can be incorporated into a power module to sequentially charge parallel supercapacitors. The boost circuit of the power module 30 illustrated in FIG. 4 can be modified to include the sequential capacitor charging circuit illustrated in FIG. 6. The sequential capacitor charging circuit includes a charge control circuit 54, switches 55a, 55n, supercapacitors 34a, 34n, and diodes 56a, 56a. The charge control circuit 54 provides an output to open and close the switches 55a, 55n. The switches 55a, 55n connect each supercapacitor 34a, 34n one at a time to the voltage output Vreg of the boost converter 51 (FIG. 4) to sequentially charge the supercapacitors 34a, 34n. Sequentially charging the supercapacitors 34a, 34n limits the capacitance on the output of the boost converter 51, which may reduce the instantaneous current draw on the output of the boost converter 51 so that the boost converter 51 operates within its current output rating. The diodes 56a, 56n connect the supercapacitors to the positive boost voltage output contact 12VOUT of the power module 30 such that the supercapacitors can provide parallel current output to the motor drive 64 (FIGS. 5A, 5B, and 7). For instance, the sequential capacitor charging circuit may be configured to charge two 1 F supercapacitors sequentially to reduce the instantaneous capacitance seen by the boost converter 51 in half compared to a boost circuit configured to charge a single 2 F capacitor. The two 1 F supercapacitors are in parallel when driving the motor 65 to effectively function as a 2 F capacitor.

FIG. 7 is a block diagram of electrically powered components of an exemplary powered surgical instrument (e.g., surgical stapler 10). The power module 30 and battery 11 can be mechanically configured as described in relation to FIGS. 3A and 3B. The battery 11 provides power to the power module 30. The electrical components of the power module 30, including the boost circuit 50 and the supercapacitor(s) 34 are referred to collectively herein as the "power system." The power system can be integral to the main housing (e.g., handle portion 20 as illustrated in FIG. 2) of a surgical instrument or separately housed which can be coupled and decoupled from a main body of the surgical instrument (e.g., as illustrated in FIGS. 3A and 3B). The power module 30 can otherwise be electrically configured similar as described in relation to FIGS. 4 through 6. As in other figures, the power module 30 is illustrated as rated at 12 V. Alternatively, the power module 30 may be rated to provide between approximately 9 V and approximately 25 V. Likewise, the battery 11 is illustrated as providing 3.3 V. Alternatively, the battery may provide between 3 V and 5 V.

The boost circuit 50 may include a power accumulator 57, a boost converter 51, a current limiter 52, and a boost converter delay circuit 53 as illustrated in FIG. 4. The optional supercapacitor charge delay circuit 36 is described in greater detail in relation to FIG. 4 and is shown outside the power module 30 in FIG. 7 as an alternative embodiment. The logic control circuit 60 of the surgical instrument can receive power from the power system directly from the battery 11, directly from the power module 30, from the battery 11 through delay circuit 36, from the power module 30 through the delay circuit 36, any combination thereof, or any single one thereof. FIG. 7 shows the logic control circuit 60 receiving power from each of the aforementioned power sources for the sake of illustration.

The logic control circuit 60 includes one or more voltage regulators 61 to provide a consistent voltage output to system control circuit(s) 62 and a motor control circuit 63. The motor control circuit 63 provides a signal to the motor drive 64 which the motor drive 64 uses to control connection of the motor 65 to the power module 30. The electrical circuitry of the surgical instrument can optionally include a current sensor 35 configured to measure current provided from the power module 30 to the motor 65. An electrical signal indicative of the current to the motor can be provided to the logic control circuit 60 and used by the motor control 63 so that the motor 65 can be driven by the motor drive 64 based in part on motor current. As illustrated, there is no delay in connection of the power module 30 to the motor drive 64. Alternatively, the motor drive 64 may be connected to the power module 30 via the delay circuit 36.

The motor 65 is coupled to a mechanical system 70 configured to provide a surgical treatment. For instance, the surgical instrument may include a surgical stapler 10 (FIG. 1) configured to provide stapling and cutting of tissue as a surgical treatment. The mechanical system 70 of the surgical stapler can include a transmission 71 coupling a drive bar 72 to the motor 65. During a firing stroke, several components of the powered surgical stapler 10 are translated longitudinally by the motor 65 to deploy staples 45 and cut tissue. The components which translate longitudinally during a firing stroke are collectively referred to as a firing assembly. The firing assembly includes the drive bar 72 (also referred to as a firing bar) and may also include a knife, an I-beam, a wedge sled, and/or other components as understood by a person skilled in the pertinent art. The surgical stapler 10 may optionally include sensor(s) 66 to various aspects of the surgical stapler 10 such as drive bar position.

As illustrated, the motor drive circuit 64 is illustrated separate from the motor control circuit 63 and separate from the logic control circuit 60. The illustration is for the purpose of showing functionality of the electronics of the surgical instrument, and the logic control circuit 60 and the motor drive circuit 64 may be separate circuits or may be integrated as a single circuit. Further, the logic control circuit 60 may be split across separate circuits. The motor control circuit 63 is configured to provide a motor setpoint signal output to the motor drive circuit 64. In one embodiment, the motor drive 64 provides a pulse width modulated (PWM) signal to the motor 65. The motor setpoint signal from the motor control circuit 63 may be indicative of a target speed of the drive bar or a duty cycle percentage of the PWM signal. The motor controller 65 is configured to provide a motor drive signal to the motor 65 such that the motor drive signal is based on the motor setpoint signal and intended to drive the motor 65 so that the firing assembly (including drive bar 72) is driven to the target speed or so that PWM signal to the motor 65 has the duty cycle percentage provided by the motor control circuit 63.

The logic control circuit 60 and the motor drive circuit 64 may include one or more processors and memory (i.e. one or more non-transitory computer-readable medium) with instructions that can be executed by the one or more processors to cause the motor control circuit 63 and the motor drive circuit 64 to drive the motor 65.

When the motor 65 drives the mechanical system 70 to provide the surgical treatment, the motor 65 receives power primarily, or solely from the supercapacitor(s) 34. The boost circuit 50 charges the supercapacitor(s) with energy from the battery 11 before and after operation of the motor 65 to provide surgical treatment and other high load conditions. The boost circuit 50 is not rated to provide sufficient current to operate the motor 65 to provide surgical treatment. For instance, the boost circuit 50 is not rated to provide sufficient current to operate the motor 65 during at least a majority of a firing stroke. In some embodiments, the boost circuit 50 is not rated to provide sufficient current to operate the motor 65 in an unloaded condition, indicative of the least amount of current required to provide a surgical treatment. In some embodiments, the boost circuit 50 may be disconnected from the supercapacitor(s) as the surgical instrument provides surgical treatment. Alternatively, the boost circuit 50 may provide limited current as the surgical instrument provides surgical treatment while the supercapacitor(s) 34 primarily power operation of the surgical instrument. For instance, current from the boost circuit 50 may be limited by a current limiter 52 (FIG. 4).

Figure 8A:
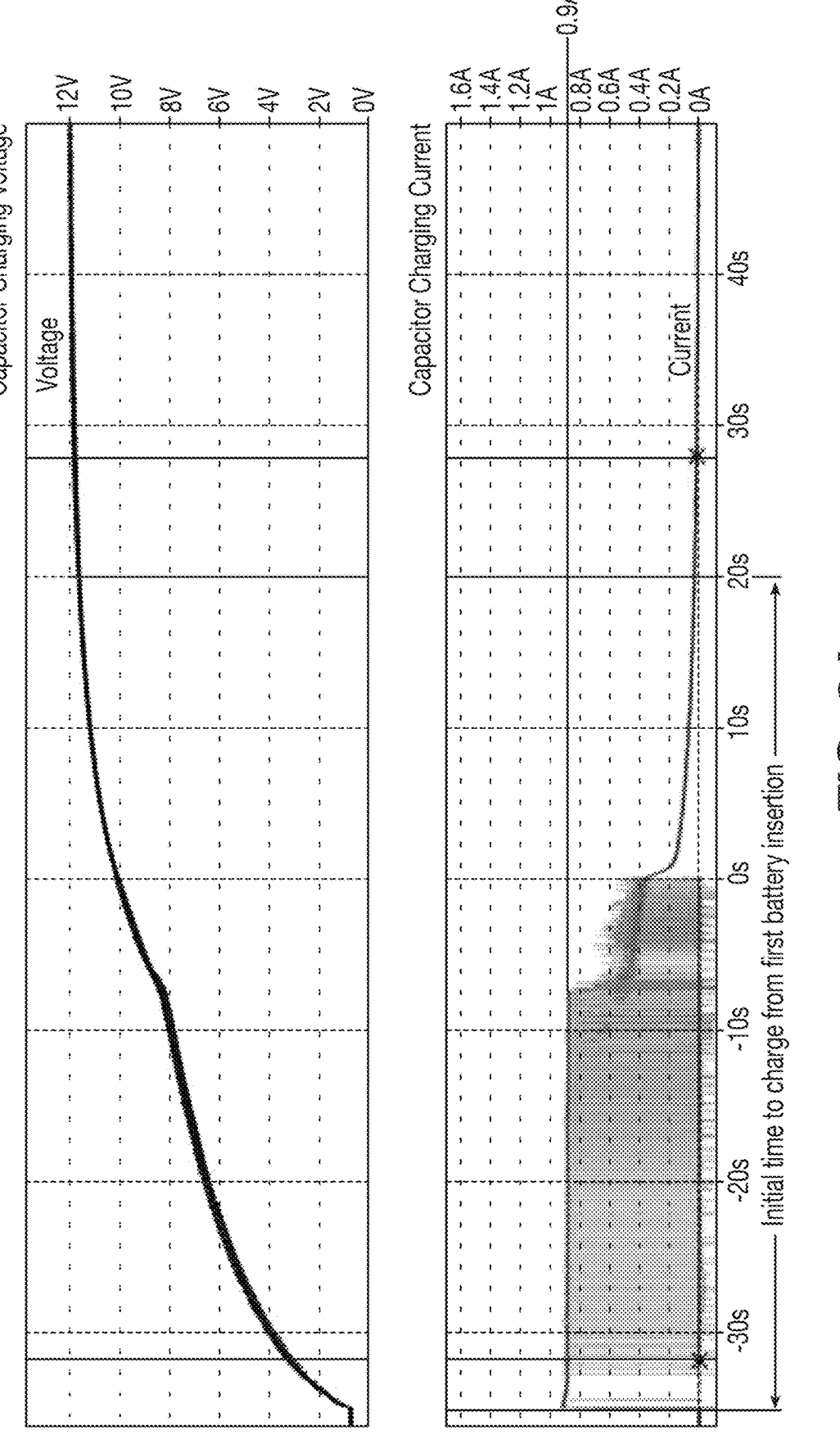
FIGS. 8A and 8B are plots of measured charging current and voltage of a supercapacitor by a boost circuit which includes an overcurrent limiter having a current limiting resistor and relying on boost converter overcurrent protection.
Figure 8B:
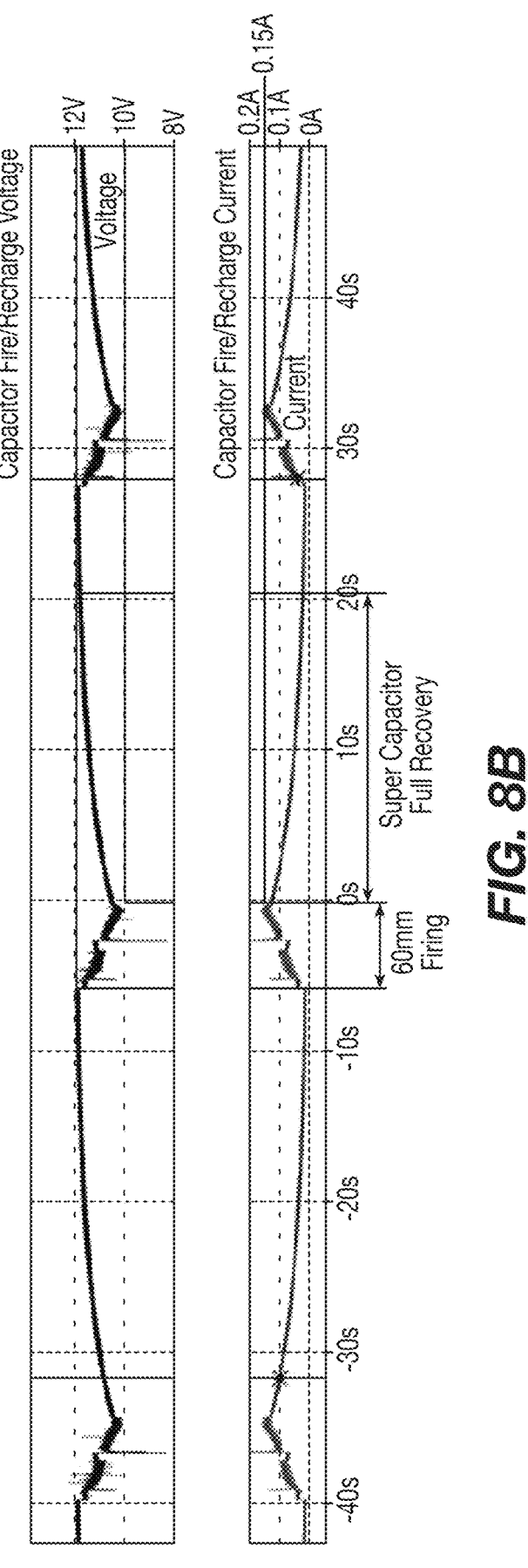

FIGS. 8A and 8B are plots of measured charging current and voltage of a supercapacitor 34 by a boost circuit 50 which includes a current limiter 52 having a 2 Ohm ((2) current limiting resistor and relying on boost converter overcurrent protection. The battery has a voltage output of 3.3 V, the boost converter 51 and thereby boost circuit has a rated voltage output of 12 V, and the supercapacitor 34 has a capacitance of 2 F. The boost converter 51 of the boost circuit includes an internal overcurrent protection circuit. In this example, five power systems, each including the printed circuit board assembly (PCBA), which includes the boost converter and related electronics, and the supercapacitor, successfully survived 20 autoclave full use cycles (273° F. for 15 minutes) with no failures. FIG. 8A shows initial charging of the supercapacitor 34. FIG. 8B shows a simulated sequence of discharging during use under a high load condition and charging by the boost circuit 50 in between usages.

FIG. 8A is a plot of voltage (top) and current (bottom) to the supercapacitor 34 during initial charging of the supercapacitor 34. The battery 11 is inserted and connected to the boost circuit 50 at the initial time period. After a short delay, the boost circuit 50 connects to the supercapacitor 34 and begins charging the supercapacitor 34. As illustrated, the supercapacitor 34 is initially at 0 V. The current draw from the boost converter 51 triggers internal overcurrent protection of the boost converter 51 such that the charge current is intermittent and limited to about 0.9 A during approximately the first 20 to 30 seconds of charging. After about 35 seconds after supercapacitor charging begins, the charge current to the supercapacitor 34 is limited by the current limiting resistor, and the current and voltage follow the expected RC time constant curves as the supercapacitor voltage approaches 12 V and the current approaches zero. The initial charge time from initial assembly to ready-to-use is about 50 to 60 seconds.

FIG. 8B is a plot of voltage (top) and current (bottom) to the supercapacitor 34 during sequential surgical treatment and recharging time periods. The supercapacitor 34 is initially charged at approximately 12 V (the rated output of the boost circuit). The voltage falls and the current increases during a simulated surgical treatment lasting approximately 5 seconds simulating a 60 mm firing stroke of a surgical stapler. The boost circuit provides current during the simulated surgical treatment that is insufficient to provide the surgical treatment on its own and insufficient to maintain the supercapacitor at 12 V. The voltage of the supercapacitor is approximately 10 V at the end of the simulated surgical treatment. Following the simulated surgical treatment, the current from the boost circuit 50 charges the supercapacitor 34 from 10 V to 12 V following the RC time constant curves. The supercapacitor 34 is charged to approximately 12 V and sufficiently charged for a subsequent charge approximately 20 to 25 seconds following the simulated surgical treatment.

Figure 9:
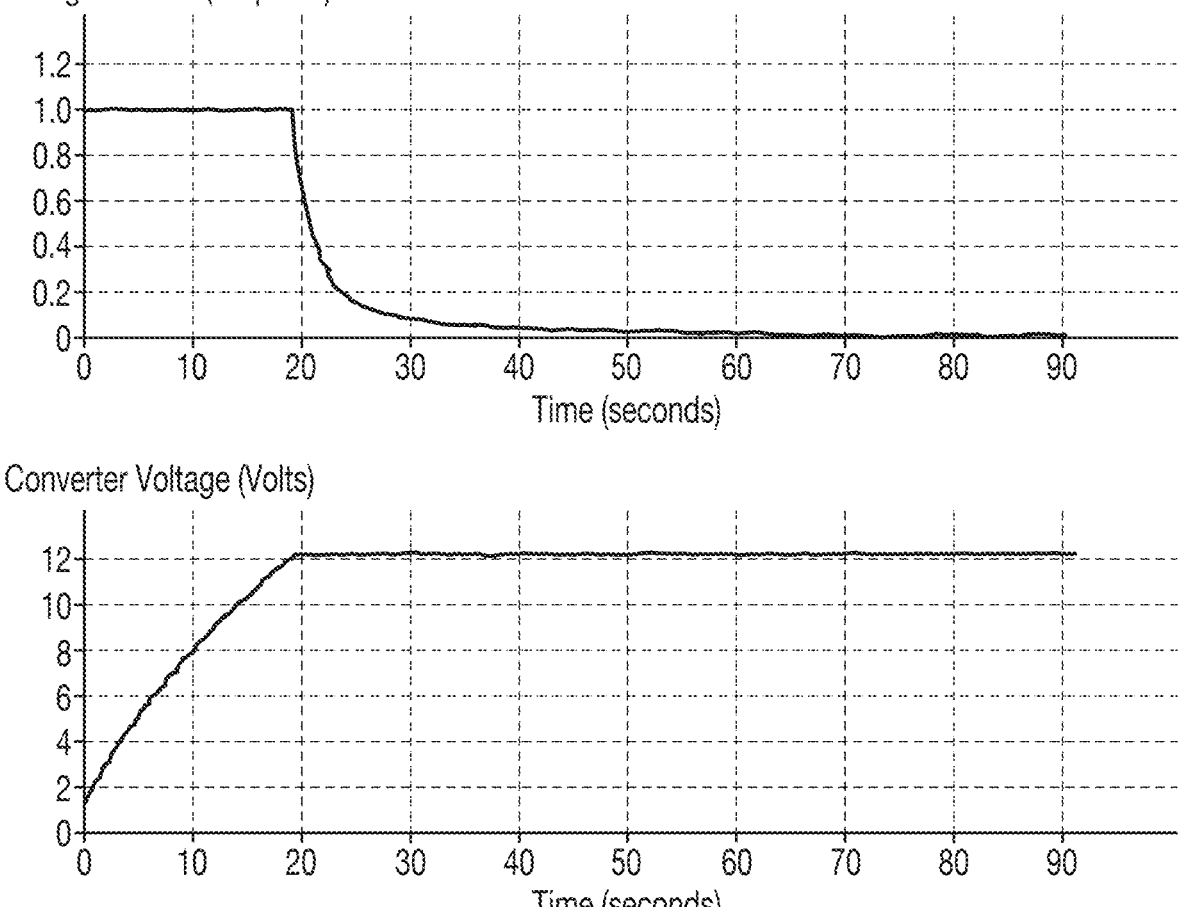
FIG. 9 includes plots of measured charge current and converter voltage during initial charging of a supercapacitor by a boost circuit which includes a current limiter including the FET.

FIG. 9 includes plots of measured charge current and boost converter output voltage during initial charging of a supercapacitor by a boost circuit 50 which includes a current limiter 52 including the FET. As in FIGS. 8A and 8B, the battery 11 has a voltage output of 3.3 V, the boost converter 51, and thereby boost circuit, has a rated voltage output of 12 V, and the supercapacitor 34 has a capacitance of 2 F.

The top graph shows the charge current to the supercapacitor as a function of time. The current limiter 52 provides a constant current of 1 A for almost 20 seconds then decays. The middle graph shows the boost converter 51 voltage as a function of time. The supercapacitor 34 voltage is approximately equal to the boost converter 51 voltage and is slightly less than the boost converter 51 voltage due to resistance in the boost circuit 50. The voltage increases approximately linearly from less than 2 V to approximately 12 V corresponding to the 20 seconds of initial charging of the supercapacitor 34. During this initial charging time period, the current limiter 52 provides a constant current output of the boost circuit 50 during supercapacitor charging when the voltage output of the boost circuit is less than the rated output of the boost circuit.

Because the boost circuit current is limited by the FET, the boost circuit requires no additional resistance to limit charge current to the supercapacitors. As such, initial charging of the supercapacitor 34 can be performed faster than when charged by a boost circuit including a current limiting resistor such as illustrated in FIG. 8A. With sufficiently low resistance in the boost circuit, the supercapacitor 34 can be charged by a constant current between surgical treatments as well. A 2 F capacitor charged by a constant current of 1 A increases in voltage by approximately 0.5 volts per second (V/s). Assuming the supercapacitor 34 voltage drops from 12 V to 10 V to provide a surgical treatment, and a constant current of 1 A is used to recharge the 2 F supercapacitor following treatment, the supercapacitor can be recharged to approximately 12 V within about 4 seconds.

The battery 11, boost converter 51, and supercapacitor 34 can be selected, as understood by a person skilled in the pertinent art, informed by the disclosure herein. The supercapacitor 34 can be selected to provide sufficient energy to operate the surgical instrument during a high load condition such as providing a surgical treatment and without undue voltage drop during the surgical treatment. The capacitance of the supercapacitor 34 should not be so high, however, that an impractically high current is required from the boost converter in order to initially charge and recharge the supercapacitor well within the typical down time before and during a surgical procedure. Boost converters with higher current output capabilities can be larger and more expensive. Further, high current output from the boost converter requires proportionally higher current output from the battery 11, which can cause the voltage of the battery 11 to sag to levels that deactivates the logic control circuit 60 and/or the boost converter 51. High battery current can also cause internal current limiting protection of the battery 11 to open, permanently deactivating the battery 11. Examples presented herein primarily focus on a power system which can be powered by a single battery cell with a voltage between about 3 V and about 5 V such as a CR123a, a CR17345, or a CR2 cell. However, examples presented herein can be modified to include two battery cells when a single cell is insufficient. If battery voltage sag is the primary issue, and the lower battery voltage output is desired for control logic, the two battery cells can be used in parallel. If boost converter current output is the primary issue, the two battery cells be used in series. For instance, the boost circuit used to charge the supercapacitor at a constant current of 1 A as shown and described in relation to FIG. 9 can be modified to charge the supercapacitor a constant current of 2 A, which reduces charge and recharge times by approximately half (i.e., about 12 seconds to charge from 0 V to about 12 V and about 2 seconds to charge from about 10 V to about 12 V).

The following clauses list non-limiting embodiments of the disclosure:

Clause 1. A surgical instrument comprising: a compartment configured to receive one or more battery cells having a first voltage rating; a boost circuit configured to receive a voltage input at the first voltage rating and provide a voltage output at a second voltage rating greater than the first voltage rating; a supercapacitor configured to be charged, via the boost circuit, to approximately the second voltage rating; and a motor configured to be powered by the supercapacitor to provide a surgical treatment.

Clause 2. The surgical instrument of clause 1, further comprising: a firing assembly configured to couple to the motor such that the motor is configured to translate the firing assembly in a distal direction to deploy staples from an end effector of the surgical instrument to provide the surgical treatment.

Clause 3. The surgical instrument of clause 1 or 2, wherein the second voltage rating is between approximately 3 and approximately 5 times the first voltage rating.

Clause 4. The surgical instrument of clause 3, wherein the second voltage rating is approximately 4 times the first voltage rating.

Clause 5. The surgical instrument of any one of clauses 1-4, wherein the boost circuit comprises a boost converter configured to convert the voltage input at the first voltage rating to the voltage output at the second voltage rating and a current limiter configured to limit current output of the boost converter to a threshold value.

Clause 6. The surgical instrument of clause 5, wherein the current limiter is configured to provide a constant current output of the boost circuit during supercapacitor charging when the voltage output is less than the second voltage rating.

Clause 7. The surgical instrument of any one of clauses 1-6, wherein the boost circuit is configured to charge the supercapacitor in a constant current mode with a constant current output to approximately the second voltage rating.

Clause The surgical instrument of clause 6 or 7, wherein the constant current output is between approximately 200 mA and approximately 2 A.

Clause 9. The surgical instrument of clause 8, wherein the constant current output is between approximately 500 mA and approximately 1 A.

Clause 10. The surgical instrument of any one of clauses 1-9, wherein the boost circuit comprises a first delay circuit configured to delay charging of the supercapacitor for a first delay time period following electrical connection of the one or more battery cells to the voltage input.

Clause 11. The surgical instrument of clause 10, wherein the boost circuit comprises a boost converter configured to convert the voltage input at the first voltage rating to the voltage output at the second voltage rating such that the voltage output achieves the second voltage rating within a soft-start time period, wherein the first delay time period is greater than the soft-start time period and less than about 1 second.

Clause 12. The surgical instrument of any one of clauses 1-11, wherein the boost circuit is configured to charge the supercapacitor to approximately the second rated voltage between approximately 10 seconds and 120 seconds following electrical connection of the one or more battery cells to the voltage input.

Clause 13. The surgical instrument of clause any one of clauses 1-12, wherein the supercapacitor has a capacitance of between approximately 1 F and approximately 3 F and a voltage rating of between approximately 12 V and approximately 15 V.

Clause 14. The surgical instrument of any one of clauses 1-13, wherein the supercapacitor has a capacitance of approximately 2 F.

Clause 15. The surgical instrument of any one of clauses 1-14, wherein the motor is configured to consume between approximately 30 J and approximately 100 J during the surgical treatment.

Clause 16. The surgical instrument of any one of clauses 1-15, wherein the supercapacitor is configured to retain a voltage of at least 50% of the second voltage rating upon completion of the surgical treatment.

Clause 17. The surgical instrument of clause 16, wherein the supercapacitor is configured to retain a voltage of between approximately 70% and approximately 90% of the second voltage rating upon completion of the surgical treatment.

Clause 18. The surgical instrument of any one of clauses 1-17, wherein the boost circuit is configured to charge the supercapacitor to approximately the second voltage rating within approximately 1 second and approximately 60 seconds following completion of the surgical treatment.

Clause 19. The surgical instrument of any one of clauses 1-18, wherein the boost circuit is configured to charge the supercapacitor to approximately the second voltage rating within approximately 2 seconds and approximately 30 seconds following completion of the surgical treatment.

Clause 20. The surgical instrument of any one of clauses 1-19, comprising: a main body comprising a handle, a shaft extending distally from the handle, and an end effector coupled to a distal end of the shaft, wherein the motor is configured to actuate the end effector to deploy staples from the end effector to provide the surgical treatment; and a power module comprising the boost circuit and the supercapacitor such that the power module is configured to mechanically and electrically couple and decouple from the main body, and wherein the power module is configured to withstand temperatures greater than 135° C. and pressures greater than 15 psi.

Clause 21. The surgical instrument of clause 20, wherein the power module is configured to withstand 270° F.

Clause 22. The surgical instrument of clause 20 or 21, wherein the power module further comprises the compartment configured to receive the one or more battery cells.

Clause 23. The surgical instrument of any one of clauses 20-22, wherein the power module comprises a pair of battery input contacts configured to make electrical connection to positive and negative terminals of the one or more battery cells and a pair of battery output contacts configured to provide connection to the positive and negative terminals of the one or more battery cells to the main body.

Clause 24. The surgical instrument of any one of clauses 20-23, wherein the power module comprises a pair of boost voltage output contacts configured to provide electrical contact to positive and negative terminals of the supercapacitor to the main body.

Clause 25. The surgical instrument of any one of clauses 20-24, wherein the power module comprises a delayed power output contact configured to provide a delayed power connection to the main body.

Clause 26. The surgical instrument of clause 25, wherein the delayed output contact is configured to provide delayed connection to the negative terminal of the one or more battery cells during a charging time period in which the supercapacitor is charged to approximately the second voltage rating following insertion of the one or more battery cells into the compartment.

Clause 27. The surgical instrument of clause 24 or 26, wherein the boost circuit comprises a visual indicator configured to indicate power connection to the main body of the delayed power output contact.

Clause 28. The surgical instrument of any one of clauses 1-27, wherein boost circuit comprises a visual indicator configured to indicate a state of charge of the supercapacitor.

Clause 29. The surgical instrument of any one of clauses 1-28, wherein the one or more battery cells consists of exactly one battery cell.

Clause 30. The surgical instrument of clause 29, wherein the compartment is configured to receive a single CR123a cell as the exactly one battery cell.

Clause 31. The surgical instrument of clause 29, wherein the compartment is configured to receive a single CR17345 cell as the exactly one battery cell.

Clause 32. The surgical instrument of clause 29, wherein the compartment is configured to receive a single CR2 lithium cell as the exactly one battery cell.

Clause 33. The surgical instrument of any one of clauses 1-28, wherein the one or more battery cells consists of exactly two battery cells.

Clause 34. The surgical instrument of any one of clauses 1-33, comprising: a plurality of supercapacitors each configured to be charged, via the boost circuit, to approximately the second voltage rating, wherein the boost circuit comprises a charge control circuit configured to sequentially charge the plurality of supercapacitors and couple at least a portion of the plurality of supercapacitors in parallel.

Having shown and described exemplary embodiments of the subject matter contained herein, further adaptations of the methods and systems described herein may be accomplished by appropriate modifications without departing from the scope of the claims.

For instance, the surgical stapler 10 can be modified to include alternative and/or additional compatible features of other surgical staplers known in the art or yet to be developed. The power system and related components such as power module 30 can be modified to provide power to another surgical instrument which presently has similar problem with battery waste as current surgical staplers. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

What is claimed is:

1. A surgical instrument comprising:
a compartment configured to receive one or more battery cells having a first voltage rating;
a boost circuit configured to receive a voltage input at the first voltage rating and provide a voltage output at a second voltage rating greater than the first voltage rating;
a supercapacitor configured to be charged, via the boost circuit, to approximately the second voltage rating; and
a motor configured to be powered by the supercapacitor to provide a surgical treatment,
wherein the boost circuit comprises a first delay circuit configured to delay charging of the supercapacitor for a first delay time period.

2. The surgical instrument of claim 1, further comprising:
a firing assembly configured to couple to the motor such that the motor is configured to translate the firing assembly in a distal direction to deploy staples from an end effector of the surgical instrument to provide the surgical treatment.

3. The surgical instrument of claim 1, wherein the second voltage rating is between approximately 3 and approximately 5 times the first voltage rating.

4. The surgical instrument of claim 1, wherein the boost circuit comprises a boost converter configured to convert the voltage input at the first voltage rating to the voltage output at the second voltage rating and a current limiter configured to limit current output of the boost converter to a threshold value.

5. The surgical instrument of claim 1, wherein the boost circuit is configured to charge the supercapacitor in a constant current mode with a constant current output to approximately the second voltage rating.

6. The surgical instrument of claim 1,
wherein the boost circuit comprises a boost converter configured to convert the voltage input at the first voltage rating to the voltage output at the second voltage rating such that the voltage output achieves the second voltage rating within a soft-start time period, and
wherein the first delay time period is greater than the soft-start time period and less than about 1 second.

7. The surgical instrument of claim 1, wherein the boost circuit is configured to charge the supercapacitor to approximately the second voltage rating between approximately 10 seconds and 120 seconds following electrical connection of the one or more battery cells to the voltage input.

8. The surgical instrument of claim 1, wherein the supercapacitor has a capacitance of between approximately 1 F and approximately 3 F and a voltage rating of between approximately 12 V and approximately 15 V.

9. The surgical instrument of claim 1, wherein the motor is configured to consume between approximately 30 J and approximately 100 J during the surgical treatment.

10. The surgical instrument of claim 1, wherein the supercapacitor is configured to retain a voltage of at least 50% of the second voltage rating upon completion of the surgical treatment.

11. The surgical instrument of claim 1, wherein the boost circuit is configured to charge the supercapacitor to approximately the second voltage rating within approximately 1 second and approximately 60 seconds following completion of the surgical treatment.

12. The surgical instrument of claim 1, comprising:
a main body comprising a handle, a shaft extending distally from the handle, and an end effector coupled to a distal end of the shaft, wherein the motor is configured to actuate the end effector to deploy staples from the end effector to provide the surgical treatment; and a power module comprising the boost circuit and the supercapacitor such that the power module is configured to mechanically and electrically couple and decouple from the main body, and wherein the power module is configured to withstand temperatures of at least 270° C. and pressures greater than 15 psi.

13. The surgical instrument of claim 12, wherein the power module comprises a delayed power output contact configured to provide a delayed power connection to the main body.

14. The surgical instrument of claim 13, wherein the delayed power output contact is configured to provide delayed connection to a negative terminal of the one or more battery cells during a charging time period in which the supercapacitor is charged to approximately the second voltage rating following insertion of the one or more battery cells into the compartment.

15. The surgical instrument of claim 12, wherein the power module comprises a pair of boost voltage output contacts configured to provide electrical contact to positive and negative terminals of the supercapacitor to the main body.

16. The surgical instrument of claim 1, wherein the one or more battery cells consists of exactly one battery cell or exactly two battery cells.

17. The surgical instrument of claim 1, comprising:

a plurality of supercapacitors each configured to be charged, via the boost circuit, to approximately the second voltage rating, wherein the boost circuit comprises a charge control circuit configured to sequentially charge the plurality of supercapacitors and couple at least a portion of the plurality of supercapacitors in parallel.

18. The surgical instrument of claim 1, wherein each of the one or more battery cells are single use battery cells.

* * * * *